United States Patent
Halaka

(10) Patent No.: US 8,843,186 B2
(45) Date of Patent: Sep. 23, 2014

(54) NON-INVASIVE REAGENTLESS GLUCOSE DETERMINATION

(71) Applicant: Folim G. Halaka, Lake Forest, IL (US)

(72) Inventor: Folim G. Halaka, Lake Forest, IL (US)

( * ) Notice: Subject to any disclaimer, the term of this patent is extended or adjusted under 35 U.S.C. 154(b) by 0 days.

(21) Appl. No.: 13/683,924

(22) Filed: Nov. 21, 2012

(65) Prior Publication Data

US 2014/0142400 A1   May 22, 2014

(51) Int. Cl.
| | | |
|---|---|---|
| A61B 5/1455 | (2006.01) | |
| A61B 5/00 | (2006.01) | |
| A61B 5/05 | (2006.01) | |
| A61B 5/145 | (2006.01) | |

(52) U.S. Cl.
CPC ........... *A61B 5/14532* (2013.01); *A61B 5/1455* (2013.01); *A61B 5/7257* (2013.01); *A61B 5/05* (2013.01)
USPC .......................................... 600/316; 600/310

(58) Field of Classification Search
USPC .................................................. 600/310–344
See application file for complete search history.

(56) References Cited

U.S. PATENT DOCUMENTS

| | | | |
|---|---|---|---|
| 3,870,612 A | 3/1975 | Flygare et al. | |
| 4,882,492 A | 11/1989 | Schlager | |
| 4,901,728 A | 2/1990 | Hutchinson | |
| 5,009,230 A | 4/1991 | Hutchinson | |
| 5,070,874 A | 12/1991 | Barnes et al. | |
| 5,119,819 A | 6/1992 | Thomas et al. | |
| 5,222,496 A | 6/1993 | Clarke et al. | |
| 5,298,967 A | 3/1994 | Wells | |
| 5,448,992 A | 9/1995 | Kupershmidt | |
| 5,459,317 A | 10/1995 | Small et al. | |
| 5,517,987 A * | 5/1996 | Tsuchiya | 600/328 |
| 5,553,613 A | 9/1996 | Parker | |
| 5,581,349 A | 12/1996 | Halaka | |
| 5,703,364 A | 12/1997 | Rosenthal | |
| 5,823,966 A | 10/1998 | Buchert | |
| 6,016,435 A | 1/2000 | Maruo et al. | |
| 6,043,492 A | 3/2000 | Lee et al. | |
| 6,044,285 A | 3/2000 | Chaiken et al. | |
| 6,061,582 A | 5/2000 | Small et al. | |
| 6,181,957 B1 | 1/2001 | Lambert et al. | |
| 6,377,828 B1 | 4/2002 | Chaiken et al. | |
| 6,424,849 B1 | 7/2002 | Berman et al. | |
| 6,424,850 B1 | 7/2002 | Lambert et al. | |
| 6,445,938 B1 | 9/2002 | Berman et al. | |
| 6,505,059 B1 | 1/2003 | Kollias et al. | |

(Continued)

OTHER PUBLICATIONS

PCT Search Report and Opinion (current case), PCT/US13/069354, Mar. 26, 2014.

*Primary Examiner* — Eric Winakur
*Assistant Examiner* — Marjan Fardanesh
(74) *Attorney, Agent, or Firm* — Clifford Kraft

(57) ABSTRACT

Non-invasive apparatus and method for determining and monitoring glucose concentrations in human subjects. Glucose level is estimated through the effect of glucose on biological cells with glucose dependencies, e.g., red blood cells. The invention is based on the interaction of such cells with oscillating electric field gradients. The response of biological cells depends on factors including shape, size, and electrical charge distribution. The field gradient causes the cells to undergo characteristic motion which is detected by light beam scattering. The autocorrelation of the scattered light is computed, and the Fourier transform (FT) is performed to produce a characteristic velocity spectrum in which the peaks are characteristic of the cell "bio-electrical" states. The glucose level is estimated through measurements of changes of FT with changes in glucose levels after calibration with standard glucose methods.

21 Claims, 10 Drawing Sheets

(56) References Cited

U.S. PATENT DOCUMENTS

| | | |
|---|---|---|
| 6,574,490 B2 | 6/2003 | Abbink et al. |
| 6,748,250 B1 | 6/2004 | Berman et al. |
| 6,841,389 B2 | 1/2005 | Novikov et al. |
| 7,050,847 B2 | 5/2006 | Ollmar et al. |
| 7,333,841 B2 | 2/2008 | Maruo et al. |
| 8,043,227 B2 | 10/2011 | Van Gogh et al. |
| 2002/0095075 A1* | 7/2002 | Madarasz et al. ............ 600/310 |
| 2005/0054907 A1 | 3/2005 | Page et al. |
| 2010/0130883 A1 | 5/2010 | Carpenter et al. |
| 2011/0208036 A1 | 8/2011 | Axelrod et al. |
| 2012/0116236 A1 | 5/2012 | Hogan |

\* cited by examiner

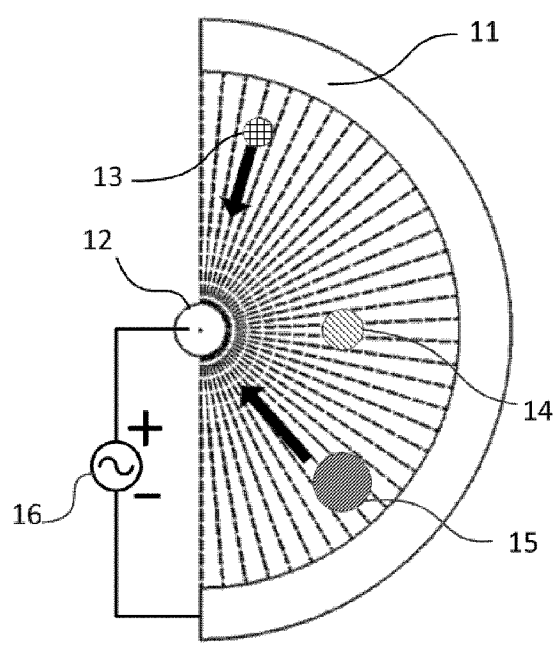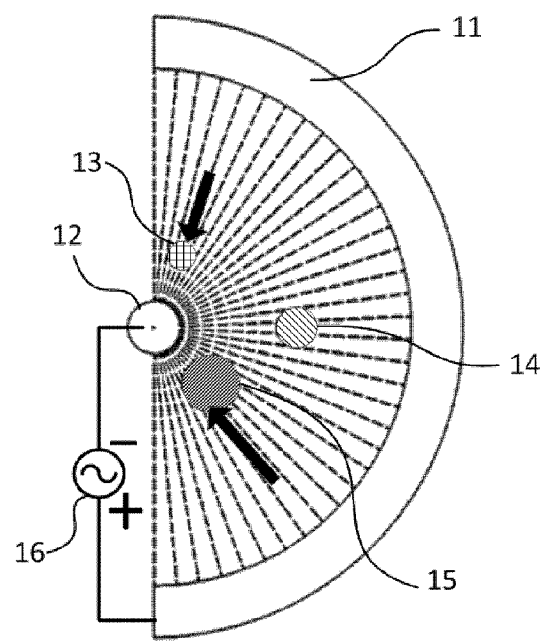
*Figure 1A*　　　*Figure 1B*

NON-INVASIVE REAGENTLESS GLUCOSE DETERMINATION

BACKGROUND OF THE INVENTION

1. Field of the Invention

The present invention relates to measuring a medical parameter and more particularly to a non-invasive glucose measurement device.

2. Description of the Prior Art

Non-Invasive (NI) blood glucose level monitoring has been pursued by many academic and industrial institutions. On-market blood glucose measurements, while achieving remarkable advances in accuracy and minimizing blood sample volume, still require blood draw. Many diabetics harbor anxiety and needle phobia to the point of interfering with timely testing. In spite of numerous publications and proposed devices, NI glucose detection devices usable by diabetics have remained elusive. Diabetes is a long term disease with well-known cardiovascular complications as well as damage to many organs such as the eyes, kidneys, and even causing amputations. A successful NI glucose measurement device would enable more frequent monitoring and compliance with medication regimes, and reduce healthcare cost.

There are numerous devices, methods, and publications in the art describing assessment of blood glucose levels. Physiological concentration of blood glucose is in the ~0.2 to ~4.5 mg/ml (~1 to 25 mM) range. Glucose exists in blood and other human body fluids such as saliva, urine, and interstitial fluid (ISF).

The Prior art of glucose measurements is divided into invasive, minimally-invasive, and non-invasive methods. Invasive methods are generally defined as those that require a droplet of blood which is then analyzed in-vitro to determine the glucose concentration. Methods requiring other body fluid, such as ISF, and/or uses less painful methods for fluid extraction, are generally called minimally-invasive. In non-invasive determinations, no blood or ISF is extracted, and the skin is not punctured. For comprehensive review, Khalil [20] provides description of the principles of many of the technologies that have been employed in the pursuit of NI glucose detection.

Numerous methods and devices have been described to take advantage of the interaction of the glucose molecule with the electromagnetic radiation. Light absorption, reflection, polarization and scattering have been exploited [1-5], particularly in the infrared (IR), near IR (NIR), and middle IR (MIR) since several glucose electronic and vibrational modes interact with radiation in these regions [9-17].

A large number of prior art articles describe the measurement of absorption, emission, polarization, scattering, and/or wavelength dependencies of the glucose molecule, seeking correlation to glucose concentration. The construction of a correlation between the measurements with the amount of glucose has received focus in prior art, as interference from and variability of other components can complicate the construction the correlation, chiefly, interference from blood and skin constituents, variability in the concentration of blood analytes, the inhomogeneity of human skin, diet, blood circulation, temperature, and drugs. Therefore, data analyses resort to the application of complex multivariate calibration for correlating of glucose concentration to the measurements [6-8].

My U.S. Pat. No. 5,581,349 describes a Method for Biological Cell and Particulate Analysis. That patent was not concerned with Glucose per se; however, the techniques taught in that patent can be used with the apparatus of the present invention to detect and monitor glucose levels in humans as will be shown.

Other US patents that are concerned with glucose measurement are herein listed:

U.S. Pat. No. 7,333,841 describes a method and device using NIR radiation on skin of a subject, receiving reflected light and calculating the glucose level from a predetermined calibrating equation. A plurality of the calibrating equations that are classified in terms of a skin thickness parameter indicative of a skin thickness parameter was used.

U.S. Pat. No. 6,748,250 describes method and system of analytes measurements by an attenuated total reflection (ATR) infrared spectroscopy method. The system comprises an input module that provides a non-invasive method in measuring analytes in a patient, such as a measurement of the glucose level and other blood analytes. The measurement is shared among a plurality of output devices such as computers, personal digital assistants (PDAs), cellular phones, etc.

U.S. Pat. No. 6,574,490 describes an apparatus and method which include multiple subsystems to improve photometric accuracy and the signal-to-noise ratio, sampling and calibration errors. Subsystems include Fourier Transform IR (FTIR) spectrometer subsystem, a data acquisition subsystem, and a computing subsystem.

U.S. Pat. No. 6,445,938 describes a device and method for non-invasive glucose measurement using Attenuated Total Reflection (ATR) infrared spectroscopy, and compares two specific regions of a measured infrared spectrum to determine the blood glucose.

U.S. Pat. No. 6,424,849 describes a method for determining the blood glucose in which skin surface is irradiated with IR and where reflected light is used for glucose level based on the intensity of the reflected IR beam.

Similarly, U.S. Pat. No. 6,424,848 describes a method of preparing skin surface and determining glucose levels using attenuated total reflection (ATR) infrared spectroscopy.

U.S. Pat. No. 6,061,582 describes method and apparatus using infrared radiation and a signal processing system. The level is determined by: (a) irradiating a portion of the test subject with near infrared radiation; (b) collecting data concerning the irradiated light on the test subject; (c) digitally filtering the collected data to isolate a portion of the data indicative of the physiological chemical; and (d) determining the amount of physiological chemical in the test subject by applying a defined mathematical model to the digitally filtered data. The collected data is in the form of either an absorbance spectrum or an interferogram.

U.S. Pat. No. 6,043,492 describes a non-invasive blood glucose meter that uses an NIR energy analyzer which includes a light filter assembly of two Fabry-Perot interferometers and a photosensor. A single crystal silicon elastic power source is used to provide the driving power of the Fabry-Perot interferometer to avoid mechanical hysteresis.

U.S. Pat. No. 6,016,435 describes a device for non-invasive determination of a glucose concentration using NIR radiation having successive wavelengths within a range of 1300 nm to 2500 nm, a light projecting unit for projecting the near-infrared radiation on a skin of the subject, a light receiving unit for receiving a resulting radiation emitted from the inside of the skin, and a spectrum analyzer.

U.S. Pat. No. 5,823,966 describes a method and an instrument for a continuous non-invasive detection using remote sensor assembly mounted in subject's ear canal continuously measures analyte concentration by detecting the infrared radiation naturally emitted by a human body using an infrared detector with a combination of adequate filters.

U.S. Pat. No. 5,703,364 describes method and apparatus using NIR with multiple wavelengths, and varying the amount of time that radiation at each wavelength illuminates the subject according to the output level of radiation at each wavelength so as to provide substantially similar detection data resolution for each of the plurality of wavelengths.

U.S. Pat. No. 5,553,613 describes a device for the non-invasive measurement of glucose. The device comprises a solid first portion having a surface profile adapted to be held against the selected body part, a source of near infrared radiation mounted in a second portion associated with said first portion such that near infrared radiation is transmitted through or reflected from said body part, a third portion containing a detector and filters to receive radiation transmitted through or reflected from said body part, to select signals generated by the pulsatile component of the absorption spectrum and to provide a ratio representative of the desired concentration.

U.S. Pat. No. 5,459,317 describes method and apparatus using IR radiation and a signal processing system. The subject is irradiated with NIR and the transmitted or reflected radiation is measured, digitally filtered, and analyzed.

U.S. Pat. No. 5,448,992, also U.S. Pat. No. 5,398,681, describe a method and apparatus based on producing a polarized-modulated laser beam, measuring a phase difference introduced, e.g., by a finger. Phase difference between a reference signal and a probe signal is also measured and data are processed to produce glucose concentration.

U.S. Pat. No. 5,222,496 describes an IR sensor and method using plurality of discrete wavelengths selected from the NIR spectrum, and transmittance or reflectance ratios for various wavelengths are performed.

U.S. Pat. No. 5,070,874 describes non-invasive determination of glucose concentration using radiation in the near infrared over a limited range of wavelengths about 1660 nanometers. The scattered or transmitted radiation is processed to derive an expression of the resulting radiation as a function of the wavelength. Curve derivatives between 1640 and 1670 nanometers are expanded and the glucose concentration is determined from the magnitude, or intensity, of the scattered or transmitted radiation at the maximum or minimum point of the second derivative.

U.S. Pat. No. 4,882,492 describes non-invasive apparatus using both diffuse reflected and transmissive infrared absorption measurements that utilize non-dispersive correlation spectrometry. Spectrally-modified near infrared light from the sample containing the analyte is split into two beams, one of which is directed through a negative correlation filter which blocks light in the absorption bands for the analyte to be measured, and the other of which is directed through a neutral density filter capable of blocking light equally at all wavelengths in the range of interest. Differencing the light intensity between the two light paths provides a measure proportional to analyte concentration.

Glucose solutions are optically active and rotate the polarization plane of linearly polarized light. The rotation angle can be used to measure the glucose concentration. However, depolarization of light occurs because of scattering by skin, and a location that possesses low scattering must be used, e.g., the anterior chamber eye [21, 22]. U.S. Pat. No. 5,009,230, and similarly U.S. Pat. No. 4,901,728, describe devices based upon the effect of glucose in rotating polarized infrared light. In order to compensate for absorption in the tissue, another two orthogonal and equal polarized states of infrared light are used.

Approaches using the techniques of photoacoustics, based on impacting sample with pulsing laser and measuring the acoustic response, have been attempted[18,19]. For example, U.S. Pat. No. 5,119,819 describes a method and apparatus that use acoustic velocity measurements, through the earlobe. The apparatus includes a transducer for transmitting and receiving ultrasonic energy pulses and a reflector for facilitating reflection of the acoustic pulses from the blood. The acoustic velocity is measured to provide a representation of the blood glucose concentration levels.

US published patent application 20050054907 describes a wearable article such as a wristwatch, which include optical and acoustic transducers. A quantum cascade laser is arranged with crystalline acoustic detectors in a photoacoustic effect measurement scheme. Laser pulses stimulate special vibrational states of glucose molecules to produce an acoustic return signal to be received at a piezoelectric detector.

Several approaches using Raman Spectroscopy have been attempted[22]. The method is based on the inelastic scattering from coupling of electronic states with vibrational/rotational modes. Fluorescence and scattering from other components can interfere with Raman signals. Raman and surface-enhanced Raman spectra show less overlap in comparison to e.g., NIR spectroscopy. For example, U.S. Pat. No. 6,424,850 (also, U.S. Pat. No. 6,181,957) describes non-invasive method which detects a Raman spectrum from illuminated aqueous humor with linear or nonlinear multivariate analysis.

U.S. Pat. No. 6,377,828 (also U.S. Pat. No. 6,044,285) describe method and apparatus where the Raman spectra emitted by the tissue are collected and analyzed to determine a concentration of analyte (glucose) present in the tissue.

Fluorescence techniques[25,26] were also used, as in U.S. Pat. No. 6,505,059.

Optical coherence tomography (OCT) [23, 24]: Utilizes light interference/time delay between backscattered light in the sample and reference light in an interferometer. OTC provides higher resolution, but temperature and motion can interference with results. US published patent application 20120116236 describes the use OCT to measure tissue dimensions affected by hydration levels and blood flow variations, which are proposed to increase the accuracy of glucose measurements.

Other techniques include impedance measurements. For example, U.S. Pat. No. 7,050,847 describes a method of measuring impedance of the skin. The measurements are repeated for different depth and at various frequencies. Skin may be exposed to salt solutions.

U.S. Pat. No. 6,841,389, also US published patent application 20100130883, describe methods of total impedance measurement of the skin, which is based on a first order correlation between the glucose concentration and the total impedance.

US published patent application 20110208036 describes a pair of coiled antennas acting as electrodes for dielectric spectroscopy measurements, placing the pair of coiled antenna in signal communication through the media, and scanning for a specific frequency range. Acquiring signals from the coiled antennas during scanning and integrating to determine analyte level.

U.S. Pat. No. 8,043,227 describes a non-invasive system and method for measuring skin hydration from thermal conductivity of the skin with a thermistor for non-invasive measurement of blood analyte detection, such as glucose, with a spectroscopic device having e.g., an infrared source which generates infrared beam and detector for detecting transmitted radiation through portion (e.g., finger) of a subject. The system for detecting blood analyte concentration may include a photoacoustic device or a metabolic heat conformation device.

Prior art techniques used for NI glucose determination show less than satisfactory correlation to glucose concentration. This can be attributed to interference from other cell/tissue components, as the measurements usually sample many components, which may be affected in different manner by variability in glucose concentration. The present invention presents features to isolate the dependency of a particular component on glucose levels, which reduces interference.

SUMMARY OF THE INVENTION

In the present invention, glucose level is estimated through the effect of glucose on certain biological cells with glucose dependencies, e.g., erythrocytes (red blood cells or RBCs). When a cell is placed in an oscillating electric field gradient, the cell undergoes characteristic motion as electrical dipoles rearrange to follow the electric field oscillations. The motion of the cell, referred to as dielectrophoresis, is characteristic mainly of the cell's size and electrical charge distribution. The motion also depends on the frequency of field oscillation, field strength, and spatial field gradient. By field gradient it is meant an electric field gradient, although other fields may be used such as a magnetic field. In this invention, the motion is detected by light scattering, typically laser light. The autocorrelation of the scattered light is computed; and, a Fourier transform (FT) is constructed to produce a characteristic velocity spectrum, in which the peaks in the FT are characteristic of cell "bio-electrical" states. Additionally procedures for correlating the FT peaks to cell conditions, particularly glycation level, are described. A brief description of the main components mentioned above is presented herein. The analytical method of using autocorrelation of scattered light from a solution containing particles with an applied non-uniform electric field is described in my U.S. Pat. No. 5,581,349 and is applied herein to a device that can measure and monitor glucose or other conditions in a human subject.

Effect of Glucose on Biological Cells:

Numerous biological cells possess glucose dependencies, e.g., RBC. Although a major focus of this invention is on applications to RBC, other cells may also be employed, particularly cells circulating in blood, e.g., macrophages, lymphocytes, platelets, etc. Glucose reacts with many cell components containing amino groups, e.g., proteins, nucleic acids, and lipids[27]. The reaction of concern is non-enzymatic: amines react with aldehydes/ketones to form Schiff bases, which can undergo further reactions (generally referred to as glycation). The degree of glycation in hemoglobin was shown to be correlated to the glucose level in serum[28]. The effect of glucose on cells properties, such as size, shape, and membrane structure, e.g., the reaction of glucose with membrane components of RBC in relation to the membrane rigidity is detailed in the literature, see for example, Hale[29], Chapter 5, and references therein. Also, studies suggest measurable dielectric properties dependency of cells on glucose[30].

Behavior of Biological Cells in Oscillating Electric Field Gradients:

As described in my U.S. Pat. No. 5,581,349, particles placed in a uniform electric field behave in a predictable manner—the familiar electrophoresis. If the particles carry a net charge, they move toward an electrode of opposite polarity; they do not move if they carry no net charge, even if the particles are polarizable. Polarizability is the ability of charges on or inside particles to move in response to the application of external electric fields, to form electric dipole (s). If the electric field is uniform, equal and opposite forces are exerted on each end of the resulting dipole, i.e., polarizability does not influence electrophoresis.

If the electric field possesses a spatial gradient, unequal forces will be experienced by each end of the dipole, leading the particle to undergo net translational motion in the direction of the maximum in the field gradient (dielectrophoresis), even if the polarizable particle is, overall, electrically neutral. Furthermore, when the applied field gradient is oscillating at certain frequencies (typically in the radio frequency (RF) range, the particle continues the translational motion in the same direction, as illustrated in FIGS. 1A and 1B, where a field gradient is formed by the choice of shape/geometry of electrodes (11 and 12). The field gradient is imposed on polarizable cells (13 and 15), forcing motion of the cells toward the anode 12 (FIG. 1A). When the polarity of the electric field is reversed (FIG. 1B), where now electrode 12 is cathode, the polarizable cells (13 and 15) experience a similar effect, but keep moving toward maximum field gradient, i.e., the cells do not reverse direction with reversal of field polarity.

Dielectrophoresis depends on biological cell conditions, particularly changes in the dielectric properties of cells, and has been the subject of numerous studies, see [35], for review. In the treatment of the effect of oscillating electric fields on biological systems, a great number of studies have focused on the detection, by electrical means, of the changes in the electrical properties of the biomolecules.

Many neutral and charged particles (e.g., biological cells) are polarizable; polarization can occur through movement of electrically charged constituents: inside the cell, on the cell surface, or by influencing the electrical double layer surrounding the cell[31,32]. For these reasons, and because they contain numerous charged molecules, most biological cells are polarizable. Furthermore, the motion is frequency-dependent, and is maximized at certain frequencies. These properties present unique and advantageous applications in the present invention, as the motion of a particular population of cells can be selected to "resonate" at certain frequencies. The motion is maximized when the frequency matches the (inverse of) the time it takes for charges to rearrange (relaxation time).

As described in my U.S. Pat. No. 5,581,349, the force exerted by the electric field on the cell depends on several factors including intrinsic properties of the cell such as size, shape, and polarizability. The force also depends on external (experimental) factors such as the field strength, gradient, and the properties of the suspending medium. The force F can be represented as:

$$F = 2\pi r^3 g \epsilon_m \nabla E^2 \quad (1)$$

Where r is the particle's radius, $\epsilon_m$ is medium's dielectric constant, and E is the electric field strength. Equation 1 indicates that the force is proportional to the volume of the cell. It can be seen that the force depends on both the field strength and on the field gradient, as $\nabla E^2$ may also be written as 2E$\nabla$E. g is a function of the electrical permittivities of the particle and the medium:

$$g = g(\epsilon_m^*, \epsilon_p^*) = \text{Re}\frac{(\epsilon_p^* - \epsilon_m^*)}{(\epsilon_p^* + 2\epsilon_m^*)} \quad (2)$$

Where Re is the real part of the complex function, and $\epsilon_p^*$ and $\epsilon_m^*$ are the complex permittivities of the particle, p, and the medium, m, respectively. A force of sufficient magnitude that acts upon a particle causes particle movement, the speed of which indicates the magnitude of the force.

As can be seen from Equation 2, the direction of motion above is for the case where the absolute values of $\in^*_p > \in^*_m$, (where the particles are more polarizable than the medium). In instances, such as here, where the particle is more polarizable than the medium, the particles migrate toward the minimum in the field gradient.

Dynamic Light Scattering:

To study the force in a quantitative manner (as manifested by the resulting velocity of the particle movement), dynamic light scattering (DLS) can be employed. In DLS, a light beam, typically from a laser, impinges on a solution of particles, and the intensity of the scattered light is measured at a specified angle. The frequency of the scattered light is Doppler shifted due to the Brownian motion of the scattering particle. The frequency shifts are related to the diffusion coefficients of the particles in the medium. DLS experiments measure the Fourier transform (FT) of these frequency shifts[33] as the time-domain autocorrelation function, $C(\tau)$.

$$C(\tau) = \langle N^2 \rangle e^{-q^2 D\tau} \quad (3)$$

Where $\langle N \rangle$ is the average number of particles per unit volume, $\theta$ is the angle between the incident and the scattered beam (defined by detector position), D is the diffusion coefficient, $\tau$ is the delay time, and q is an experimental constant related to the light arrangement and the medium:

$$q = \frac{4\pi n}{\lambda} \sin\frac{\theta}{2} \quad (4)$$

Here, n is the refractive index of the medium, $\theta$ is the scattering angle, and $\lambda$ is the wavelength of the light beam. The diffusion coefficient D for a spherical particle is:

$$D = \frac{kT}{6\pi\eta r} \quad (5)$$

where k is the Boltzmann constant, T is the absolute temperature, $\eta$ is the viscosity of the medium and r is the particle's radius. Formula (5) is presented for reference even though particles such as red blood cells are not spherical. Similar relationships exist for non-spherical particles It is known that time autocorrelation functions of Brownian motion are smooth exponential functions and are characteristic of the diffusion coefficients of the scattering species, which are used as a measure of their size from the diffusion coefficient. Except for single (monodisperse) systems, $C(\tau)$ data will be a superposition of multiple exponentials. This drawback has historically restricted DLS from application to complex mixtures such as blood.

Dielectrophoretic Dynamic Light Scattering (DDLS):

The imposition of an oscillating electric field gradient on the particles introduces significant features into DLS. A directed (non-Brownian) motion introduces modulations into the exponentially decaying $C(\tau)$ measured in DLS experiments which adds new information. The resulting function $C'(\tau)$ is modulated since it incorporates sinusoidal (or other) oscillations onto $C(\tau)$ [34]:

$$C'(\tau) = C(\tau)\cos(q \cdot v\tau) \quad (6)$$

where v is the directed velocity exhibited by the particle under the application of the field gradient. Equation 6 analyses may be simplified by the FT after removal of the component of the spectrum due to the Brownian motion, $C(\tau)$. $C(\tau)$ is acts as a background dampening factor for the oscillation. Removing $C(\tau)$ produces new "v-space" spectrum. The new spectrum, henceforth DDLS, provides both qualitative and quantifiable means to measuring cell movement, and thus to cell's state, and can be used to predict cell glycation when relevant cell properties, e.g., size, shape, membrane structure, and electrical charge distribution, depend on glucose concentration.

The present invention utilizes discernible spectral features of Equation 6 as a function of conditions of particular cells, e.g. red blood cells. Because properties of such cells change with glucose levels, it follows, as predicted from Equations 1, 3, and 6, that the v-space spectrum can be utilized to indicate the glucose levels from changes to these features.

Additionally, the peaks in the FT spectrum may be also assigned to particular species. Each polarizable population present would, in principal, contribute a peak in the spectrum. By choice of frequency, electrode configuration and other experimental embodiments, it is possible to achieve an experimentally distinguishable response from different constituents in a mixture as described in my U.S. Pat. No. 5,581,349.

The present invention presents significant advantages for the measurement and monitoring of glucose, among them the detection scheme and the use of dynamically differentiated light scattering signal. This can be revealed from examining the parameters of equations 3 and 6. An important practical characteristic of these equations is that the "static" scattering, e.g., time-invariant scattering, can be removed using appropriate logic and data analysis tools without removing significant details from collected data.

The ability to target and identify the response of a particular population of cells is an important advantage of the present invention. This is accomplished through the response of cells to the particular frequency of the applied field gradient since many cell populations respond to particular frequency ranges [31, 32]. This enables the targeting of a particular cell population to be preferentially affected by the choice of the applied oscillating field gradient frequency. This contrasts prior art techniques which sums the response from all components in the sample and thus renders such prior art techniques susceptible to interfering biological material.

Another advantage of the present invention can be seen from the penetration of electric fields into dielectric material, e.g., skin, finger nails, and the like which enables non-invasive characterization of diseases caused by, or manifested in, changes in cell conditions. Additionally, no reagents are consumed by application of the present invention; it is reagentless.

BRIEF DESCRIPTION OF THE DRAWINGS

Attention is now directed to several illustrations that show features of the present invention.

FIGS. 1A-1B show the effect of an electric field gradient on biological cells.

Figure 2:
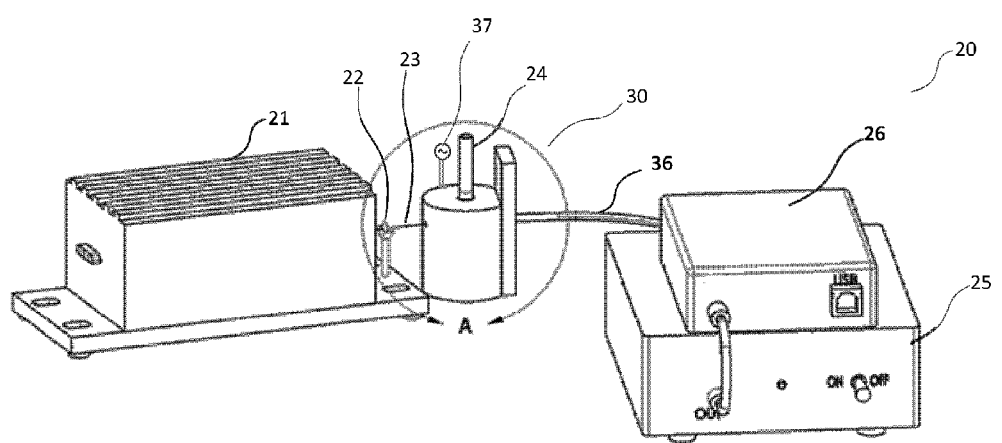
FIG. 2 shows components of a "desktop" DDLS instrument setup according to the present invention.

Several drawings and illustrations have been presented to aid in understanding the present invention. The scope of the present invention is not limited to what is shown in the Figures.

DESCRIPTION OF THE PREFERRED EMBODIMENT

Turning to FIGS. 1A-1B, the effect of an oscillating electric field gradient on biological cells can be seen. The field gradient is formed by the choice of geometry and positioning of electrodes (11 and 12). The field gradient forces polarizable cells (13 and 15) toward the anode 12 (FIG. 1A). The direction of motion of cells is represented by corresponding arrows. When the polarity of the electrical field is reversed (FIG. 1B), polarizable cells (13 and 15) keep moving in the same direction (toward maximum field gradient) Unpolarizable cell 14 is unaffected. The electric field lines are presented as the dashed lines in FIGS. 1A and 1B.

An embodiment of the present invention contains a device with electrodes similar to the electrodes in FIGS. 1A and 1B, where the electrodes are connected to an oscillating power supply for creating an oscillating electrical field gradient with frequency preferably between 0 Hz and 100 GHz, more preferably in the radio frequency (RF) range between 3000 Hz to 3 GHz, and finally more preferably between 10 KHz and 100 MHz. The frequency of the oscillating power supply may be adjusted to maximize the movement of a particular cell population. The oscillating power supply (16) is selected to be capable of providing an electrical potential with amplitude at least from approximately 1 volt p-p up to at least 1000 volts p-p. The oscillating power supply, in combination with the electrode arrangement, provides a field gradient between 100 V/cm$^2$ and 10$^9$ V/cm$^2$, and preferably between 10$^3$ V/cm$^2$ and 10$^5$ V/cm$^2$. The high magnitudes of the field gradients are possible because the gap between the electrodes is small. In an embodiment of the present invention, the electrodes are comprised of noble metal, e.g., platinum (Pt) and may be shielded by a suitable insulator. The edge of one of the electrodes may be displaced from the edge of the other electrode so as to create a non-uniform field. Preferably, the electrodes are arranged as a ring or partial ring in a manner similar to that depicted in FIGS. 1A-1B or FIG. 6. In a preferred embodiment, the electrodes are aligned so that a part of the incident light beam (23 in FIG. 2, 60 in FIG. 7) reflects from the tip of an electrode (or elsewhere) to create a heterodyne mode known in the art [33].

In various embodiments, the electrodes may be shielded, preferably for non-invasive measurements on the (human) body and for application to non-invasive detection of glucose level changes by applying field gradient across specific areas of human body preferably using the device described in FIGS. 4-7.

Figure 3:
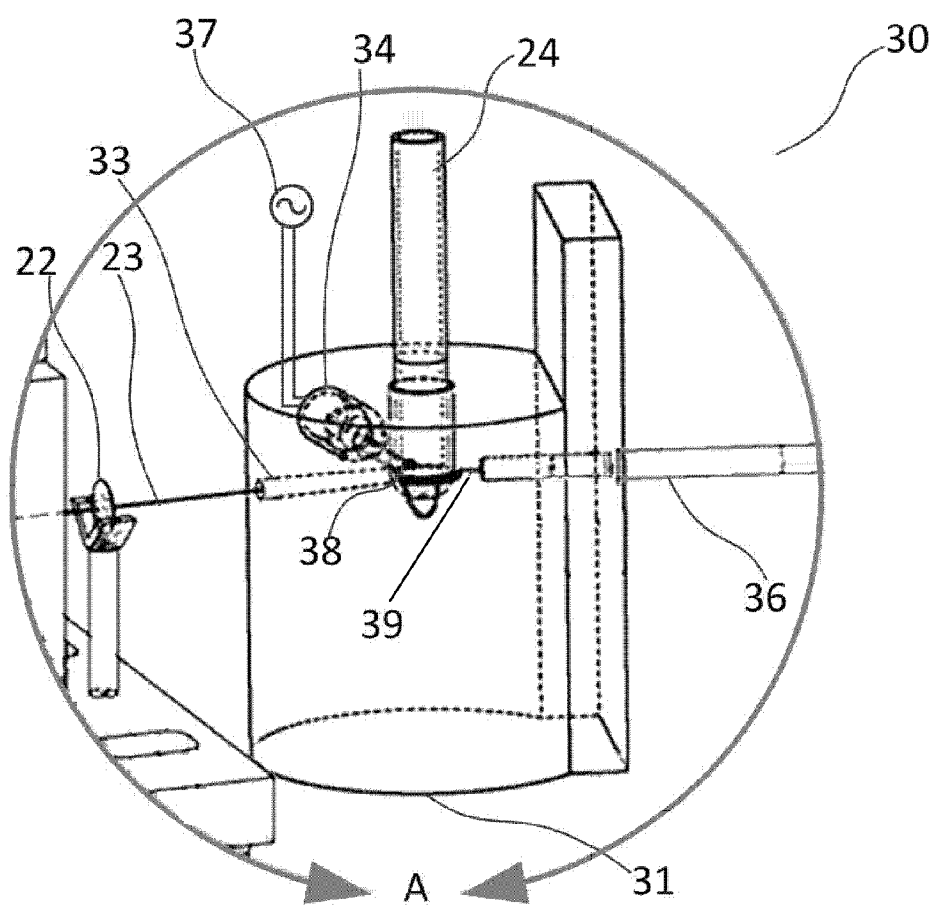
FIG. 3 is an enlarged view of the scattering vessel assembly depicted in FIG. 2.
Figure 4:
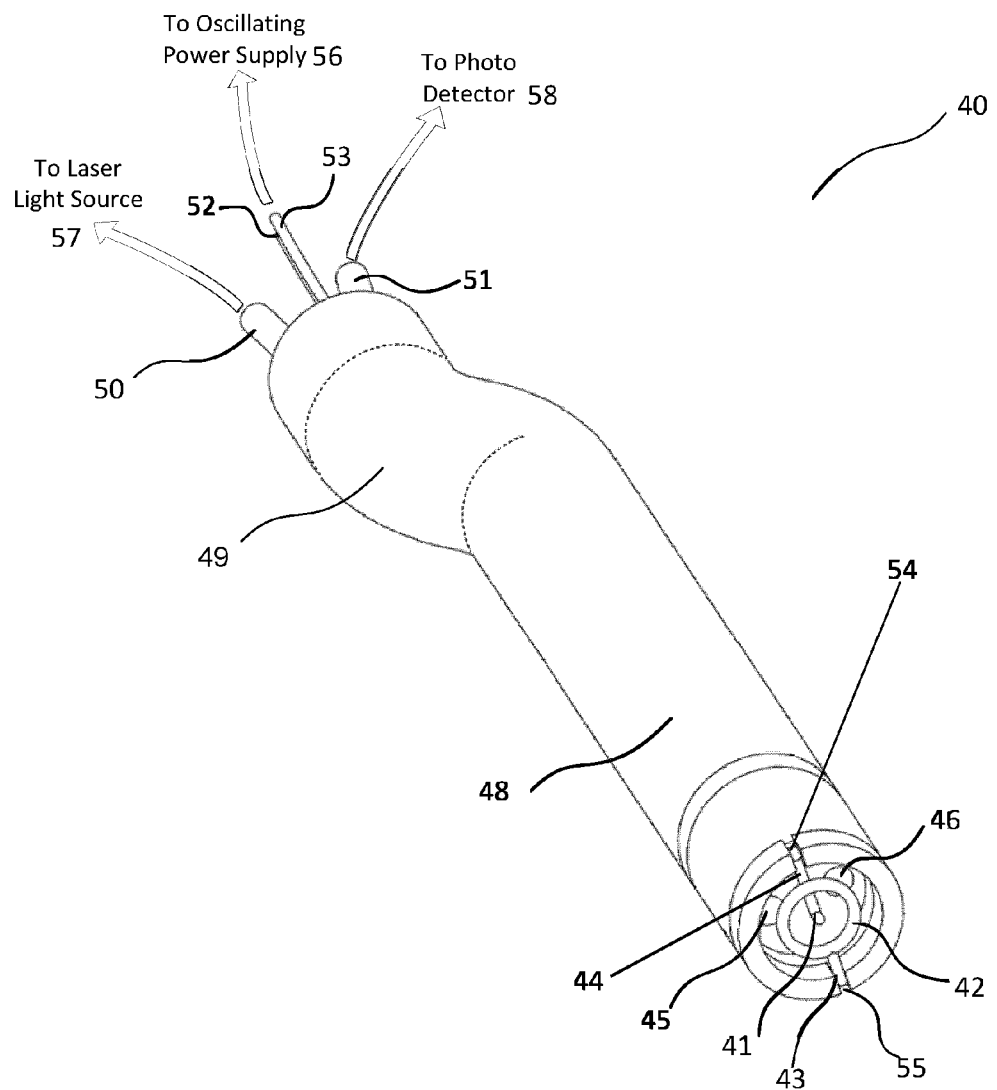
FIG. 4 is shows the components of a non-invasive device according to the present invention.

FIG. 2 shows a desktop DDLS instrument 20 to characterize biological cells according to the present invention. The instrument components include a laser 21 to produce a collimated incident beam of light 23, which may be focused through lenses 22. The incident laser beam may alternatively be conveyed using an optic fiber. Laser beam 23 enters sample vessel assembly 30 which is further detailed in FIG. 3. In FIG. 3, a laser beam 23 enters an opening 33 in support 31 where the beam impinges on sample vessel 24 containing biological material of interest. Part of the beam 23 scatters off electrode 38 to generate a heterodyne mode that allows easy detection and correlation. An electric field gradient is created between electrodes 38 and 39 by oscillating power supply 37 which is connected to the electrodes through connector 34. Scattered light 27 is collected in optical fiber 36.

Returning to FIG. 2, optical fiber 36 connects to a photodetector 25, which may be a device that uses the photoelectric effect to convert radiant energy into an electrical signal such as a photodiode or a phototube. Photodetector 25 is preferably a photon counting photomultiplier tube (PMT) or preferably an avalanche photodiode (APD). Any light detecting method or device is within the scope of the present invention. The electrical signal from the photodetector enters digital correlator 26 which constructs the autocorrelation function (Equations 3 and 6). The output of the digital correlator is digitized usually by an analog to digital converter (A/D converter) and analyzed by logic, typically in a processor, to correlate the autocorrelation functions to glucose levels from stored calibration curve or to take a Fourier Transform (FT) and correlate spectral peaks. A microprocessor, microcontroller, digital signal processor or other processor with appropriate programming is generally used for such tasks. Preferably the analysis uses the Fourier Transform FT as discussed above. Fourier Transforms can conveniently be realized by algorithms known as Fast-Fourier Transforms (FFT). Various windowing and zero-padding techniques known in the art may be used to aid in taking the FT.

The system shown in FIG. 2 can be used to characterize the parameters of oscillator frequency, field strength (and oscillator voltage), gradient strength, beam wavelength, laser power and other necessary parameters such as refractive index and viscosity of the subject material.

Characterization of the above parameters enables the utilization of these parameters in the non-invasive operation of the present invention. For in-vitro measurements of cells in e.g., extracted blood sample, the sample is placed in the sample vessel 24 where the electrodes generate an electric field gradient after energizing the oscillating power supply 37. The sample vessel walls may be of glass, quartz, or clear plastic. The sample vessel may be immersed in a bath of refractive index-matching fluid, e.g., silicon oil. The temperature may be controlled by a thermoelectric (Peltier) device, such as those that can be obtained from TE Technologies of Traverse City, Mich., USA. An example of oscillating power supply 37 may consist of an electrical function generator producing an oscillating electrical signal (typically sinusoidal) which can be amplified by a broad-band amplifier and fed to two electrodes 38 and 39. The field gradient is achieved by arrangement of the two mentioned electrodes in a fashion similar to that depicted in FIGS. 1A, 1B and FIG. 6. Those familiar with the art may construct field gradients in several other electrode configurations. The electrodes may be configured to produce a uniform gradient to minimize field gradient inhomogeneity in the scattering volume. In a preferred embodiment, the field gradient can range from $10^4$ V$^2$/m$^3$ to $10^{20}$ V$^2$/m$^3$ and preferably from $10^{12}$ to $5 \times 10^{15}$ V$^2$/m$^3$. Preferred oscillating electric field gradient strengths are chosen to cause polarization of the biological cells in specified areas of the body.

Figure 5:
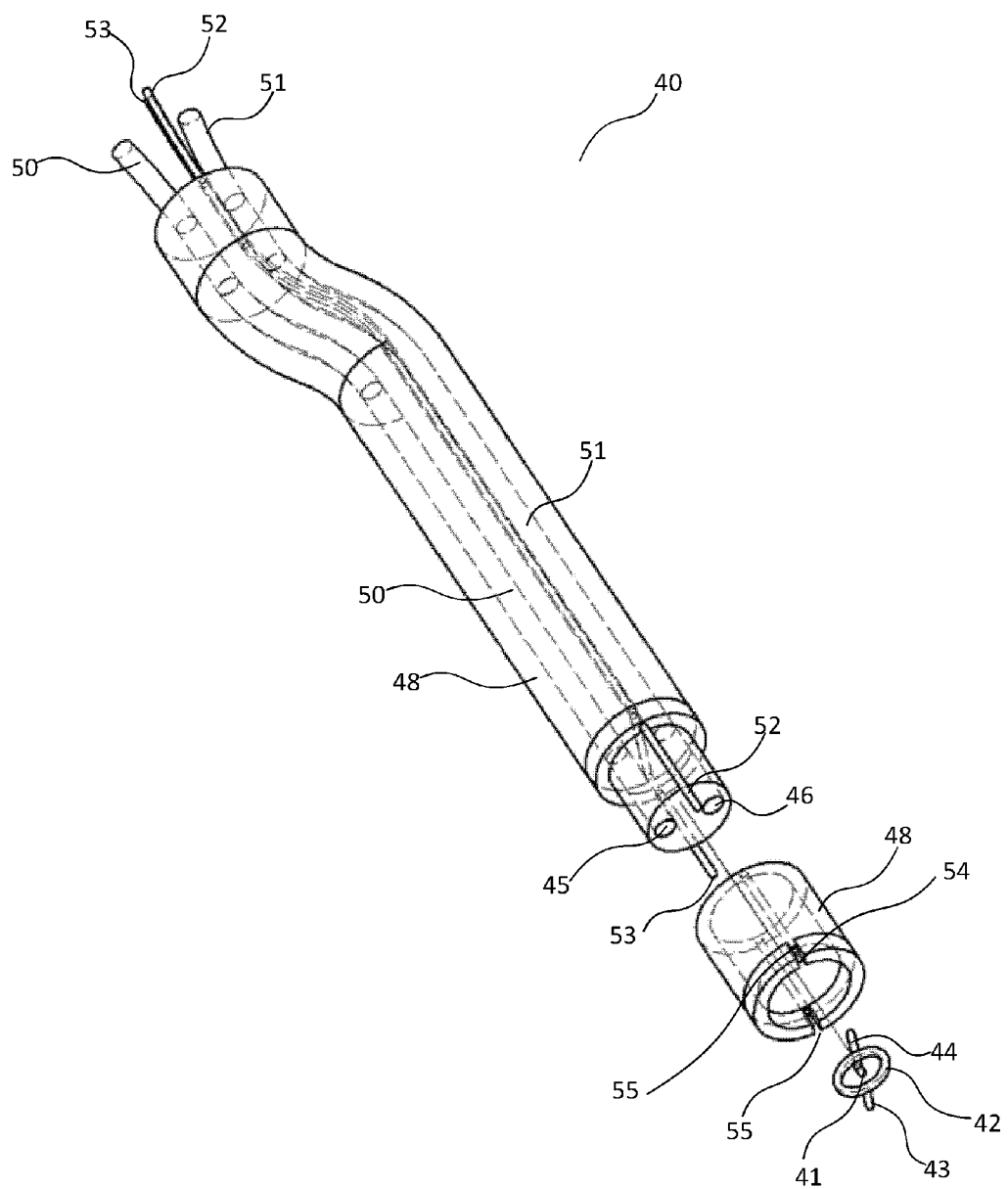
FIG. 5 is an exploded view of the non-invasive device depicted in 4 showing internal components.

FIGS. 4-7 show an embodiment for a device 40 for non-invasive measurement of glucose contained in biological fluids, e.g., blood in a non-invasive manner according to the present invention. FIG. 5 shows an exploded view of the device in FIG. 4 with the inner components outlined with dashed lines. Device 40 includes two electrodes 41 and 42 arranged to generate an electric field gradient. The oscillating electric power supply 56 (not shown in) is capable of generating an oscillating electrical field by supplying sufficient voltage to achieve sufficient field gradients. Electrode connectors 43 and 44 are seated in grooves 54 and 55 and connect to the oscillating electrical power supply 56 through connectors 52 and 53. The oscillating electrical power supply 56 (not shown) may include an electrical function generator which generates a sinusoidal electrical wave, a square or triangular wave, or any other waveform, which is fed to an electrical signal amplifier to adjust the electrical waves' amplitude. For safety, the voltage between the tip and ground should not exceed recommended safe medical levels. If the tip is properly insulated, at least 40 V p-p may be used. The maximum allowed voltage will vary from country to country based on national safety standards. The connection is achieved by assembling the electrodes into guiding grooves 54 and 55. When the oscillating electric power supply 56 is energized, the oscillating electrical voltage supplied to the two electrodes 41 and 42 causes the creation of an oscillating electric field gradient.

Figure 6:
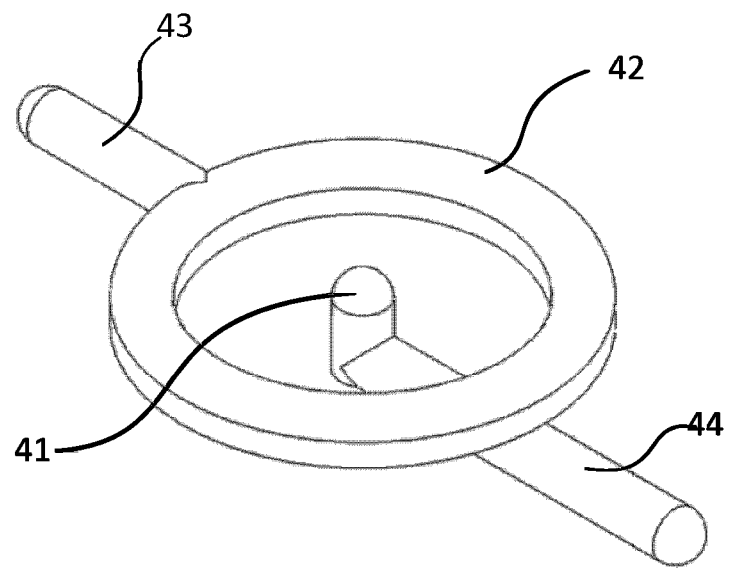
FIG. 6 is an exploded view of the electrode assembly shown in FIG. 5.

The electrodes are further illustrated in FIG. 6, where electrodes 41 and 42, due to their geometrical ring or partial ring shape, create a field gradient when connected to the electric power supply. Other electrode configurations, such as the configuration in FIGS. 1A-1B, may also be used. The electrodes and fiber optics configuration at the end that interacts with specific areas of body may be optionally thermostated to allow performing measurements at specified temperatures.

Figure 7:
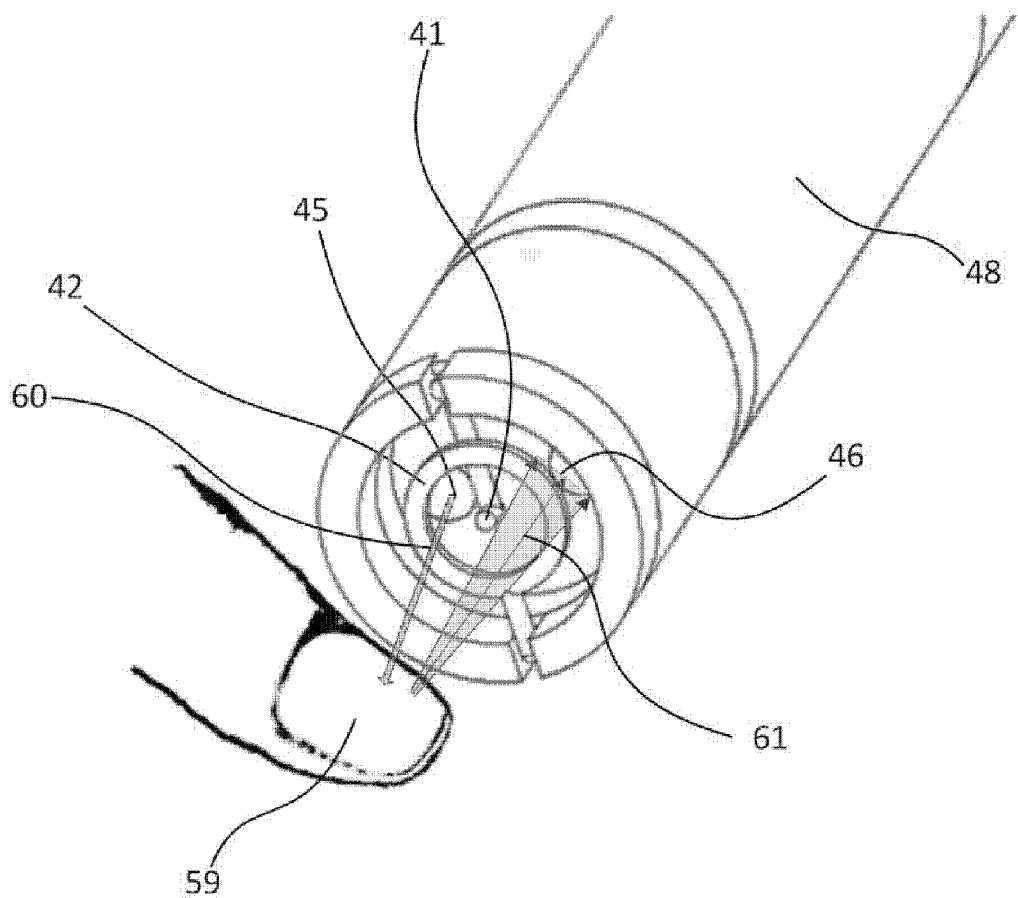
FIG. 7 is a detailed view of the application of the device in FIG. 6 to non-invasive measurements on the thumb nail area.

Referring to FIG. 7, electrodes 41 and 42 can be placed in a specified position, e.g., distance and orientation, with respect to a specified area of the body, such as finger nail, forearm, cheek, palm, stomach skin, earlobe, eye's humor etc. It is preferred that the two electrodes be safely insulated, and that the distance from the specific body part be as small as possible, preferably between 0 and 5 mm. A clamp may be used to repeatably position the electrodes in the specified position with respect to the specified area of the body.

Returning to FIG. 4, the light source 57 (not shown) is preferably a laser, and preferably a solid state, single mode laser (such as may be provided by e.g., Quartron, Inc., Chino, Calif., USA). While a laser is the preferred light source, any light source is within the scope of the present invention. Light source 57 may produce collimated light with a wavelength in the near UV, visible, or near infrared regions. Different wavelengths can be used with different tissue or sample types. The incoming light can be coupled through an optical fiber cable 50, where the light beam is transmitted to impinge on the sample of interest. Incident light is scattered by the sample, and the scattered light can be transmitted through optical fiber cable 51 to a photodetector 58, such as a PMT or an APD (such as that provided by e.g., Hamamatsu Photonics K.K., Hamamatsu City, Japan). Additionally, flat surface Gradient-index (GRIN) lenses 45 and 46 may also be used for efficient coupling of the incident light and the scattered light to the optical fiber cables 50 and 51, respectively. Optical fiber cables and electrode wires are preferably enclosed in a flexible conduit for ease of orienting and positioning of the device with human body parts. At one end, a flexible part of conduit 49 encases the wires connecting electrodes 41 and 42 to the oscillating electrical power supply 56, and the optical fiber cables 50 and 51 to light source 57 and photodetector 58 respectively. At the other end of the conduit, a rigid portion 48 encases the electrode and fiber optics in a fixed configuration to ensure repeatability and ease of positioning with respect to the specified body part. Lens or optical fiber end 45 focuses the beam on the target. Lens or optical fiber end 46 collects the scattered light.

Scattered light from the interaction of the incident light beam with specific areas of the body is affected by the motion of biological cells, e.g., in blood, ISF, or serum. Since the cells are also affected by the electric field gradient, the scattered light contains information pertaining to the scattering cells. As discussed previously, the motion of cells whose conditions are affected by glucose concentration, e.g., RBC can indicate their glycation state. Therefore, analysis of the scattered light produces correlation to the status of cell glycation. The scattered light, collected at a specified angle θ, is converted by a photodetector 58, to electric signals. The electric signals may be digitized by an analog-to-digital converter as known in the art, and may be integrated with the photodetector and a correlator to a construct time autocorrelation functions. The photodetector 58 is preferably a photon-counting PMT or an APD.

The autocorrelator output may be used by a computer or other processor with logic to further analyze the autocorrelation functions by the construction of a FT and storing the resulting velocity spectra for comparison with calibration data or as databases.

FIG. 7 shows an enlarged schematic of the bottom end of an embodiment of the present invention which details the application of the device to non-invasive measurement by positioning the device on or above the thumb nail area 59. Electrodes 41 and 42 are positioned at close distance from a translucent area of the body, e.g., thumb nail 59. With the oscillating power supply energized, an oscillating electric field gradient is created in the tissue under the thumbnail. Incident light beam 60 impinges on and is scattered by cells that respond to the applied field gradient. The scattered beam 61 enters fiber optic through 46 and travels to the photodetector. To ensure repeatability, the position of the device with respect to the body part, e.g., the thumb nail, may be aided by marking and clamping accessories. A computer or other processor with appropriate logic and software algorithms may be utilized to perform the data analysis previously discussed.

The present invention provides a method for non-invasive indication of glucose levels in the body by measuring the effect of glucose on the response of biological cells to the application of an oscillating electric field gradient on a specified area of the human body. Preferred areas of the body are characterized by being slightly opaque or translucent to allow for moderate penetration of the light beam into the tissues and the escape of the scattered light from areas of the body with biological cells-containing fluids such as blood, serum, and ISF. Examples of suitable areas of body include, but are not limited to, the finger nails, forearm, cheek, palm, stomach skin, earlobe, or the eye. It is preferable that the same areas be repeatedly used.

A preferred method for data analysis and display of DDLS measurements includes constructing a normalized function, $C'_{norm}(\tau) \quad [(C'(\tau)_\tau - C'(\tau)_{\tau=\infty})/[C'(\tau)_{\tau=0} - C'(\tau)_{\tau=\infty}]$, where $C'(\tau)_{\tau=0}$ is the value in the first channel of the correlator, and $C'(\tau)_{\tau=\infty}$ is the value in the delay channel. The spectrum due to the Brownian motion may be estimated by curve-fitting $C'_{norm}(\tau)$ to an exponential function which is the functional form of $C(\tau)$. The curve fitting may be accomplished by, for example, non-least square minimization procedure using special software or commercial software such as Microsoft's EXCEL Solver add-in (Microsoft, Redmond, Calif., USA). The oscillations due to DDLS (the term $e^{-iq\cdot v\tau}$ in Equation 7) can be obtained by dividing $C'_{norm}(\tau)$ by the exponential estimation of $C(\tau)$. This can be important in removing the static scattering components in addition to reducing the occurrence of low frequency peaks in the FT. The FT analysis can then be applied to the resulting function, and preferably, the FT is performed on the functional form: $[(C_{norm}'(\tau)/C_{norm}(\tau))-1]$ to render the oscillations symmetrical around zero and to minimize high frequency ripples (or side lobes) due to the presence of sharp truncation functions. In some cases, "zero filling or padding", or window functions may be used to improve the resolution in the FT and remove artifacts such as those caused by Gibbs phenomena known in the art. The velocities in the FT spectrum may be normalized (using the applied field strength and gradient) to correlate measurements under different conditions. The FT thus, under specified conditions, presents a "finger print" of the sample. Peaks in the FT may be assigned to particular components, e.g., RBC. The peaks can then be used to study changes to the specified components due to glucose variations which indicate glycation extent. The data analysis scheme just described is preferred, although other analyses and algorithms familiar to those skilled in the art may be applied.

An important component of the present invention is to the construct a "calibration" to correlate the measurements made with the instrument of the invention with established glucose measurements using validated glucose meters. In one embodiment, the calibration measurements are used to construct a look-up table, or "calibration look-up table", to retrieve glucose values corresponding to peaks in the FT spectra. Alternatively, a mathematical equation that can be called a "calibration equation" can be constructed from fitting observed data: peaks in the FT spectra, treated as indicated above, vs. glucose concentration determined by validated glucose level meters. This correlation can be used to non-invasively calculate the glucose concentration from measurements using the present invention.

In an embodiment of the current invention, a method of correlating non-invasive DDLS measurements to validated glucose meter measurements is presented, thus establishing a calibration data set or "calibration procedure". A possible calibration uses the following steps:

i- measure the glucose level of a sample using current validated glucose level meter at physiologically relevant glucose levels;
ii- use the device described in FIGS. 4-7 to:
  a. determine the time-dependent autocorrelation function $C(\tau)$ without the application of the electric field on the specific area of body per the data analysis scheme mentioned above;
  b. generate an oscillating electric field gradient of a specified frequency, electric field strength and field gradient and apply to the specific area of body;
  c. measure the time-dependent autocorrelation function $C'(\tau)$ under the influence of the applied field gradient per the data analysis scheme mentioned above;
iii- repeat steps i- and ii- for other biologically relevant glucose concentrations; and,
iv- construct a calibration from pairs of DDLS measurement data vs. validated glucose meter measurements.

An alternative to step ii-a, above, is the curve fitting of an exponential function, which is the functional form of the autocorrelation function to obtain $C(\tau)$, to the data collected in step ii-c for use with the analysis discussed above. Other functional forms, e.g., multiple exponentials, polynomials or other smooth functions may also be used as fitting function.

An alternative to step iv-, above, is the construction of calibration equation from the calibration table data.

An embodiment for use of the current invention provides a method for non-invasive indication of glucose levels in a subject, accomplished by measuring the effect of glucose on the response of specific biological cells, e.g., RBC, to the application of an oscillating electric field gradient on a specified area of the body using the device of FIGS. 4-7, and including the following steps:

i- determine the time-dependent autocorrelation function, $C(\tau)$, without the application of the electric field on said area of body;
ii- generate an oscillating electric field gradient of a specified frequency, electric field strength and field gradient on said area of body;
iii- measure the time-dependent autocorrelation function, $C'(\tau)$, under the influence of the applied field gradient, and;
iv- determine the glucose level concentration from the DDLS measurement using either a look-up calibration table or by substitution into a calibration equation.

An alternative to step i-, above, is the curve fitting of an exponential or other functions to the data collected in step ii- to as discussed above.

Another embodiment of the present invention is its application to non-invasive detection of glucose changes by applying DDLS measurements to biological fluids other than blood, e.g., saliva or urine, using the embodiment described in FIG. 2.

The methods above may be used to construct a calibration table or calibration mathematical equation for individual patients. The measurements may be performed under specified conditions of time of day, metabolic state, and ambient temperature and humidity.

Additionally, a globalized correlation may be established where a look-up table or a mathematical function may serve as reference for glucose level determination for a group of patients. Sub-populations of patients may be identified that share similar calibration characteristics.

In addition to non-invasive glucose level detection, the present inventions may be applied to other areas such as the identification of biological cells, biological macromolecules and polymeric substances.

For example, the present invention affords a method by which biological cells are identified by their FT spectrum under normalized conditions of electric field strength, electric field gradient, applied light source, frequency, and the like. The response of the biological cells to the field gradient and the subsequent autocorrelation function measurement, data analysis procedures and FT spectral analysis can follow steps similar to those described in the above embodiments and using devices similar to those of FIGS. 2 and 7. Calibration methods include assignment of FT spectral features to normal biological cells, which may be used to identify such normal cells. Some biological cells are known to be "not-normal" by current medical conventions, and may also be characterized by applying procedures as outlined above. Conditions that would render a cell not-normal may include cancer, metabolic stress, aging, genetic diseases, and infection by bacteria, viruses or other infectants. Initially, the FT spectral response described is correlated with established or validated identification of biological cells with the methods presented in the present invention. The construction of a repository of correlated data allows the use of the present invention to detect cell conditions, and thus offers diagnosis of biological cell maladies including cancer, aging, genetic diseases, infectious diseases and other stresses.

Similar devices and methods may be applied by the present invention to the detection of infectious organisms such as bacteria and viruses.

The present invention may also be applied to the identification of macromolecules. By macromolecule it is meant a molecule of molecular weight above 50,000 Daltons, and preferably in the range of 100 kilo Daltons to 100 Giga Daltons. Of particular interest is the application to the detection of DNA molecules, particularly with the polymerase chain reactions (PCR). PCR produces elongated DNA macromolecules which are identifiable by the present invention, and using the embodiments depicted in FIGS. 2 and 7.

There are applications of the present invention to non-biological macromolecules and polymers, including industrial polymers and latex manufacturing, with methods and devices similar to those presented herein.

EXAMPLES

Example 1

Figure 8:
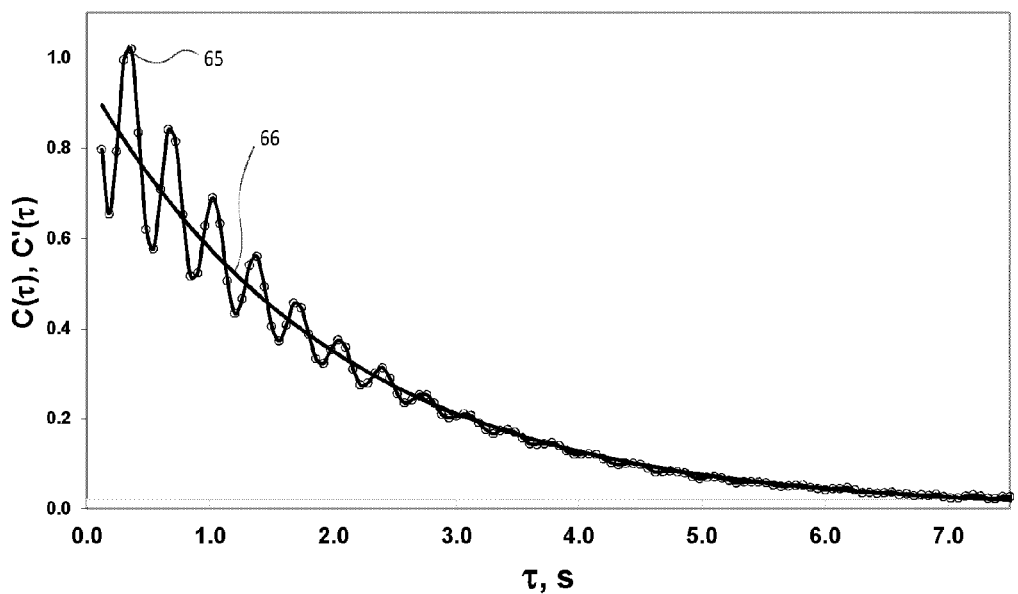
FIG. 8 is a graph showing an example of the effect of the application of an oscillating field gradient on the autocorrelation function of a suspension of $1\times10^{-6}$ gram/ml latex particles, of approximately 4.1 micron diameter in distilled water.

An example that illustrates the use of the device in 0 and associated data analyses is presented in FIG. 8, as applied to a suspension of $1 \times 10^{-6}$ gram/ml 4.1 microns latex particles. The particles were suspended in distilled water (conductivity~30µ Semen/cm). Other parameters used: applied voltage: 40 V (nominal, peak-to-peak, as measured from the output of RF amplifier); frequency: 350 kHz; $\tau$: 60 microseconds; and, $\theta = 90°$. For display, the normalized heterodyne autocorrelation functions were constructed from the correlator's raw data using the equation: $C'_{norm}(\tau) = [(C'(\tau)_\tau - C'(\tau)_{\tau=infinity}]/C'(\tau)_{\tau=0} - C'(\tau)_{\tau=infinity})$, where $C'(\tau)_{\tau=0}$ is the value in the first channel of the correlator, and $C(\tau)_{\tau=infinity}$ is the value in the correlator's delay channel. In FIG. 8, is 66 is normalized $C'(\tau)$, and 65 is $C(\tau)$ per above description. $C(\tau)$ in this case was obtained from curve fitting of $C'(\tau)$ to an exponential function.

Example 2

Figure 9:
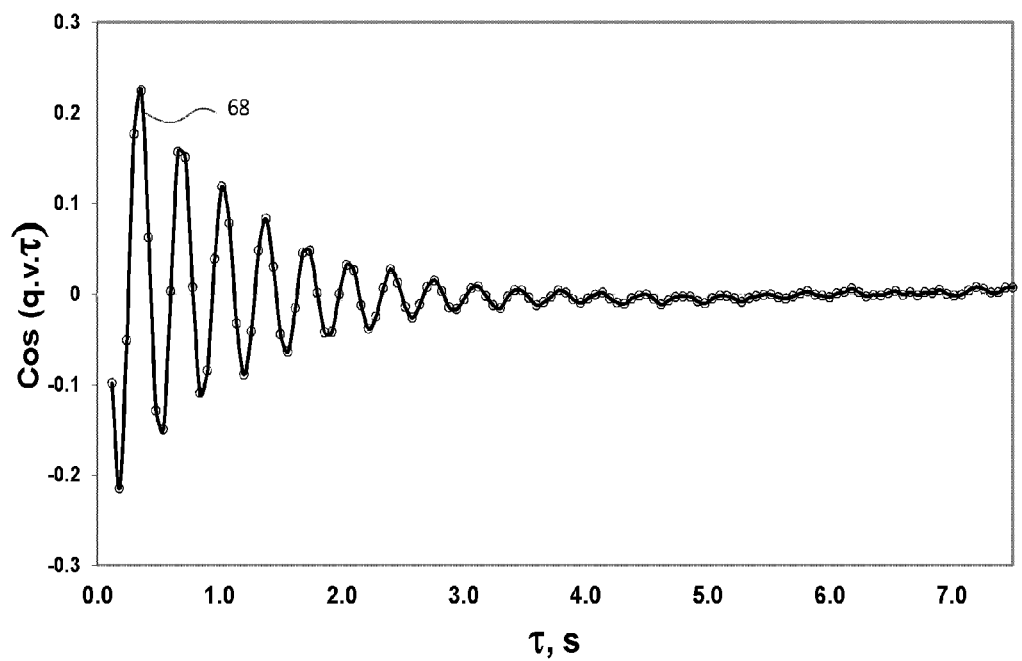
FIG. 9 is a graph of DDLS oscillations extracted from the data in FIG. 8 showing the oscillations due to the application of the field gradient.

The data in Example 1 were further analyzed by extracting the oscillations due to the application of the field gradient per the analysis schemes of this invention. FIG. 9 shows the extracted oscillations. The oscillations 68 in FIG. 9 were calculated as $[C'_{norm}(\tau) - 1]$ to aid in the removal of spurious peaks in the FT. The FT showed a single peak, as expected. Improvements in the FT analysis may be accomplished by a weighting scheme, e.g., by dividing by the dampening factor $C'(\tau)$ as known in the art[36,37].

Example 3

Figure 10:
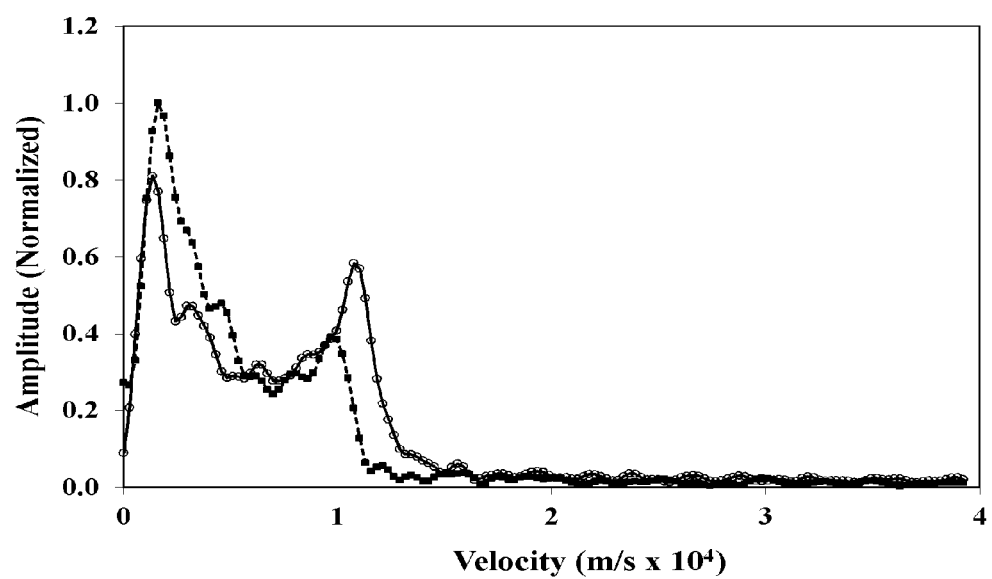
FIG. 10 is an example of the FT application to produce v-space spectrum as applied to a solution of yeast cells. 0.5 gram of Baker's yeast was suspended in 100 mL water and centrifuged at 2000 g for 10 minutes. The supernatant was discarded and the pellet resuspended (by vortexing) in 100 ml of water. The process was repeated once more and the suspension was. The measurements and data analysis were carried out as outlined herein.

FIG. 10 shows the application of the device presented in FIG. 2 and the data analysis procedures of the present invention as applied to a yeast cell mixture, with separate measurements using frequencies of 300 kHz and 500 kHz. A sample of Baker's yeast (0.5 gram in 100 ml water) was suspended in water and centrifuged at 2000 g for 10 minutes. The supernatant was discarded and the pellet resuspended (by vortex) in 100 ml of water. The process was repeated once and the suspension was used in the measurements, with other conditions similar to those in FIGS. 8-9. The isolated oscillations were extracted, and the FT (velocity domain) spectra of the oscillations are displayed. Trace 75 represents the spectrum from the application of oscillating field gradient of 300 kHz, while trace 76 is the spectrum resulting from the application of 500 kHz. Peak positions can be seen to depend on the frequency employed.

Several descriptions, illustrations and examples have been presented to aid in understanding the present invention. One with skill in the art will realize that numerous changes and variations may be made without departing from the spirit of the invention. Each of these changes and variations is within the scope of the present invention.

REFERENCES CITED

1. Heise H. M., "Non-invasive monitoring of metabolites using near infrared spectroscopy: state of the art" *Hormones Metabolism Research*, 28, 527-534 (1996).
2. Coté G. L., "Noninvasive optical glucose sensing—An overview" *Journal of Clinical Engineering*, 22, 253-259 (1997).
3. Waynant R. W. and Chenault V. M., "Overview of non-invasive fluid glucose measurement using optical techniques to maintain glucose control in diabetes mellitus" *LEOS Newsletter* 4: 3-6 (1998).
4. Khalil O. S., "Spectroscopic and clinical aspects of non-invasive glucose measurements", *Clinical Chemistry* 45, 165-177 (1999).
5. McNichols R. J. & Coté G. L., "Optical glucose sensing in biological fluid: an overview". *Journal of Biomedical Optics*, 5, 5-16 (2000).
6. Haaland D. M. and Thomas E. V., "Partial least-squares methods for spectral analyses 1: relation to other quantitative calibration methods and the extraction of qualitative information", *Analytical Chemistry* 60, 1193-1202 (1988).
7. Heise H. M., Marbach R., Janatsch G. and Kruse-Jarres J. D., "Mulitivariate determination of glucose in whole blood by attenuated total reflection infrared spectroscopy", *Analytical Chemistry* 61, 2009-2015 (1989).
8. Martens H. and Naes T., "Multivariate Calibration"; Wiley, Chichester (1991).
9. Robinson M. R., Eaton R. P., Haaland D. M., Koepp G. W., "Thomas E. V., Stallard B. R. and Robinson P. L., "Noninvasive glucose monitoring in diabetic patients: a preliminary evaluation", *Clinical Chemistry* 38, 1618-22 (1992).
10. Burmeister J. and Arnold M. A., "Evaluation of measurement site for non-invasive blood glucose sensing with near-infrared transmission spectroscopy", *Clinical Chemistry* 45, 1621-1627 (1999).
11. Blank T. B., Ruchti T. L., Malin S. F. and Monfre S. L., "The use of near-infrared diffuse reflectance for the non-invasive prediction of blood glucose levels", *IEEE Laser Electro-Optics Society Newsletter* 13, 9-12 (1999).
12. Heise H. M., Marbach R., Koschinsky T. H. and Gries H. M., "Non-invasive blood glucose sensors based on near-infrared spectroscopy", *Artificial Organs* 18, 439-447 (1994).
13. Marbach R., Koschinsky T. H., Gries H. M. and Heise H. M., "Non-invasive glucose assay by near-infrared diffuse reflectance spectroscopy of the human inner lip", *Applied Spectroscopy*. 47, 875-881 (1993).
14. Heise H. M. and Marbach R., "Effect of data pre-treatment on the non-invasive blood measurement by diffuse reflectance near-IR spectroscopy", *SPIE Proceedings* 2089, 114-115 (1994).

15. Jagemann K. U., Fischbacher C., Danzer K., Muller U. A. and Mertes B., "Application near infrared spectroscopy for non-invasive determination of blood/tissue glucose using neural network", *Zeitschrift für Physikalische Chemie* 191S, 179-190 (1995).
16. Fischbacher C., Jagemann K. U., Danzer K., Muller U. A., Papenkrodt L. and Schuler J., "Enhancing calibration models for non-invasive near-infrared spectroscopic blood glucose determinations", *Fresenius Journal of Analysis Chemistry* 359, 78-82 (1997).
17. Muller U. A., Mertes B., Fischbacher C., Jagemann K. U. and Danzer K., "Non-invasive blood glucose monitoring by means of new infrared spectroscopic methods for improving the reliability of the calibration models", *International Journal of Artificial Organs* 20, 285-290 (1997).
18. 75. Zhao Z., Nissilä S., Ahola O. and Myllylä R., "Production and detection theory of pulsed photoacoustic wave with maximum amplitude and minimum distortion in absorbing liquid", *IEEE transactions on Instrumentation and Measurement*, 47, pp. 578-583, (1998).
19. 76. Zhao Z. and Myllylä R., "Photoacoustic determination of glucose concentration in whole blood by a near-infrared laser diode", *Biomedical Optoacoustics II, Proceedings of SPIE*, 4256, pp. 77-83, 2001.
20. Khalil O. S., "Non-Invasive Glucose Measurement Technologies: An Update from 1999 to the Dawn of the New Millennium", *Diabetes Technology and Therapeutics*, 6, 660-697 (2004).
21. Rabinovitch B., March W. F. and Adams R. L., "Noninvasive glucose monitoring of the aqueous humour of the eye" *Diabetes Care* 5, 254-265 (1982).
22. Tarr R. V. and Steffes P. G., "The non-invasive measure of D-glucose in ocular aqueous humor using stimulated Raman spectroscopy", *IEEE Laser Electro-Optics Society Newsletter* 12, 22-27 (1998).
23. Huang D., Swanson E. A., Lin C. P., Schuman J. S., Stinson W. G., Chang W., Hee M. R., Flotte T., Gregory K., Puliafito C. A. and Fujimoto J. G., "Optical coherence tomography" *Science* 254, 1178-1181 (1991).
24. Larin K., Larina I., Motamedi M., Gelikonov Y., Kuranov R. and Esenaliev R., "Potential application of optical coherence tomography for non-invasive monitoring of glucose concentration", *Proceedings of SPIE* 4263, 83-90 (2001).
25. Schultz J. S., Mansouri S. and Goldstein I. J., "Affinity sensor: A new technique for developing implantable sensors for glucose and other metabolites", Diabetes Care 5, 245-253 (1982).
26. Ballerstadt R. and Schultz J. S., "Competitive-binding assay method based on fluorescence quenching of ligands held in close proximity by a multivalent receptor", *Analytical Chemistry Acta* 345, 203-212 (1997).
27. Singh R., Barden A., Mori T. and Beilin L., "Advanced glycation end-products: a review", Diabetologia, 44, 129-146 (2001).
28. Rohlfing C. L., Wiedmeyer H. M., Little R. R., England J. D., Tennill A., and Goldstein D. E., "Defining the relationship between plasma glucose and hba1c", *Diabetes Care*, 25, 275-278 (2002).
29. Hale, J., "The Thermal Fluctuations of Red Blood Cells", *Ph.D. Thesis*, University of Exeter, Exeter, Devon EX4 4QJ, United Kingdom (2010).
30. Abdalla S., "Effect of erythrocytes oscillations on dielectric properties of human diabetic-blood," *AIP ADVANCES*, 1, 012104 (2011).
31. Pohl H. A., in "Dielectrophoresis," *Cambridge University Press* (1978).

I claim:
1. A non-invasive glucose measuring apparatus comprising:
an elongated housing configured to present an oscillating, non-uniform electric field onto a predetermined part of a human body;
said housing containing first and second electrodes, the first electrode being arcuate; the second electrode being substantially centered in said arcuate first electrode, wherein said electrodes are configured to generate the non-uniform electric field near the arcuate electrode and the center electrode when the electrodes are connected to an oscillating electrical power source;
a light source
said elongated housing also configured to present a collimated light beam generated by the light source onto said predetermined part and to direct light scattered from said part into a detector;
a processor in communication with said detector, said processor executing a program that produces an autocorrelation related to said scattered light;
said program comparing said autocorrelation, or a function of said autocorrelation, against a predetermined calibration to determine a glucose level.
2. The non-invasive glucose measuring apparatus of claim 1 wherein said light source is a laser.
3. The non-invasive glucose measuring apparatus of claim 1 wherein said detector is a photomultiplier or a photo-diode.
4. The non-invasive glucose measuring apparatus of claim 1 wherein said oscillating, non-uniform electric field is powered by an oscillating power supply.
5. The non-invasive glucose measuring apparatus of claim 4 wherein said oscillating power supply supplies an oscillating voltage of between approximately 1 volt and 1000 volts.
6. The non-invasive glucose measuring apparatus of claim 4 wherein said oscillating power supply supplies a voltage oscillating at a frequency between approximately 0 Hz and 100 GHz.
7. The non-invasive glucose measuring apparatus of claim 1 wherein said light source is a laser; said detector is a photomultiplier or a photo-diode; and said oscillating, non-uniform electric field is powered by an oscillating power supply.
8. The non-invasive glucose measuring apparatus of claim 7 wherein said processor, said laser, said detector and said oscillating power supply are separate from said elongated housing, and wherein light is supplied from said laser to said elongated housing and from said elongated housing to said detector by fiber optics, and a voltage is applied from said oscillating power supply to said probe by an electrical conductor to form said non-uniform field.
9. The non-invasive glucose measuring apparatus of claim 1 wherein said program that produces said autocorrelation function uses a correlator device.
10. The non-invasive glucose measuring apparatus of claim 1 wherein said program performs a Fourier Transform on said autocorrelation.
11. The non-invasive glucose measuring apparatus of claim 1 wherein said non-uniform electric field has a gradient between approximately 10 volts/cm$^2$ and approximately $10^9$ volts/cm$^2$.
12. The non-invasive glucose measuring apparatus of claim 1 wherein said oscillating, non-uniform electric field is sinusoidal.
13. The non-invasive glucose measuring apparatus of claim 1 wherein said predetermined calibration function is constructed by forming a plurality of autocorrelations or functions of autocorrelations with said apparatus at different glu- cose levels and comparing each to a calibrated glucose level taken close to the same time on the same subject with a validated glucose measuring device.

14. The non-invasive glucose measuring apparatus of claim 1 wherein said non-uniform electric field is formed by a first and second electrode, said first electrode being a ring or partial ring; said second electrode being located at a point in proximity to a center-point of said ring.

15. The non-invasive glucose measuring apparatus of claim 1 further comprising an electrode producing said non-uniform electric field and wherein a portion of said collimated light beam reflects off of said electrode into said detector to create a heterodyne.

16. A method of in-vivo measurement of a glucose level in a bio fluid using an elongated housing comprising:
    exposing a non-uniform, oscillating electric field onto a predetermined part of a human body containing said bio-fluid, said field originating from first and second electrodes in said elongated housing; wherein the first electrode being arcuate; the second electrode being substantially centered in said arcuate first electrode, wherein said electrodes are configured to generate a non-uniform electric field near the arcuate electrode and the center electrode;
    scattering a light beam from said bio-fluid into a detector;
    processing an output from said detector to form an auto-correlation;
    computing a mathematical transform of said autocorrelation to produce a velocity spectrum;
    comparing at least one peak in said velocity spectrum against a calibration to determine a glucose level in said bio-fluid.

17. The method of claim 16 further comprising:
    producing said calibration by measuring glucose levels in test subjects using said probe and comparing said glucose levels with levels measured using a validated glucose meter.

18. A non-invasive glucose elongated housing comprising an electrode arrangement adapted to produce a non-uniform electric field and to present said field onto a target external to the elongated housing;
    said elongated housing adapted to provide a collimated light beam onto the target, and to gather scattered light from the target, supplying said scattered light to a detector; said elongated housing also adapted to reflect a portion of said collimated light beam from said electrode arrangement and to also supply that to the detector;
    said housing containing a non-linear electric field generator comprising a first and second electrodes, the first electrode being arcuate; the second electrode being substantially centered in said arcuate first electrode, wherein said non-linear electric field generator produces a non-uniform electric field near the arcuate electrode and the center electrode when the electrodes are connected to an oscillating electrical power source;
    a processor, separate from the elongated housing, in communication with said detector, said processor executing a program that produces an autocorrelation related to said scattered light;
    said program comparing said autocorrelation, or a function of said autocorrelation, against a predetermined calibration to determine a glucose level.

19. The non-invasive glucose elongated housing of claim 18 wherein said autocorrelation is transformed into a velocity spectrum.

20. The non-invasive glucose elongated housing of claim 19 wherein at least one peak in said velocity spectrum is compared against a calibration to produce a glucose level estimate.

21. A dielectrophoretic dynamic light scattering probe for measuring a property of a bodily fluid comprising:
    an elongated, substantially tubular housing having a proximal and distal end, said housing containing a first and second fiber optic, the first fiber optic adapted to convey a collimated light beam to a location proximate said bodily fluid from the distal end to the proximal end of said probe; the second fiber optic conveying scattered light from the proximal end to the distal end of said probe;
    said housing containing a non-linear electric field generator comprising a first and second electrodes, the first electrode being arcuate; the second electrode being substantially centered in said arcuate first electrode, wherein said non-linear electric field generator produces a non-uniform electric field near the arcuate electrode and the center electrode when the electrodes are connected to an oscillating electrical power source;
    said housing and said non-linear electric field generator adapted to be placed near an extremity of a human patient, wherein the non-linear electric field generator is configured to present said non-linear electric field into the human extremity; the first fiber optic configured to present said collimated light beam into the human extremity, and said second fiber optic configured to convey scattered light from the human extremity to a detector, said detector electrically coupled to a processor that computes an autocorrelation and determines said property.

* * * * *